United States Patent
Barna et al.

(10) Patent No.: US 10,517,779 B2
(45) Date of Patent: Dec. 31, 2019

(54) ABSORBENT ARTICLE WITH POCKET PROVIDING ENHANCED CONTROL

(71) Applicant: Kimberly-Clark Worldwide, Inc., Neenah, WI (US)

(72) Inventors: Nicole J. Barna, Appleton, WI (US); Sara Stabelfeldt, Appleton, WI (US); David F. Bishop, Appleton, WI (US); Nancy E. Dawson, Appleton, WI (US); Robert M. Hill, Neenah, WI (US); Eric D. Johnson, Larsen, WI (US); Paul A. Weber, Larsen, WI (US); Georgia L. Zehner, Larsen, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 407 days.

(21) Appl. No.: 15/511,065

(22) PCT Filed: Sep. 30, 2014

(86) PCT No.: PCT/US2014/058232
§ 371 (c)(1),
(2) Date: Mar. 14, 2017

(87) PCT Pub. No.: WO2016/053285
PCT Pub. Date: Apr. 7, 2016

(65) Prior Publication Data
US 2017/0246058 A1 Aug. 31, 2017

(51) Int. Cl.
*A61F 13/49* (2006.01)
*A61F 13/84* (2006.01)
(Continued)

(52) U.S. Cl.
CPC ........ *A61F 13/84* (2013.01); *A61F 13/49011* (2013.01); *A61F 13/51498* (2013.01);
(Continued)

(58) Field of Classification Search
CPC .......... A61F 13/49466; A61F 13/51798; A61F 13/5622; A61F 13/627; A61F 13/84;
(Continued)

(56) References Cited

U.S. PATENT DOCUMENTS

| 3,865,110 A | 2/1975 | Traverse |
| 5,308,345 A | 5/1994 | Herrin |

(Continued)

FOREIGN PATENT DOCUMENTS

| EP | 1 688 117 A1 | 8/2006 |
| GB | 2298354 A1 | 9/1996 |

(Continued)

*Primary Examiner* — Catharine L Anderson
(74) *Attorney, Agent, or Firm* — Kimberly-Clark Worldwide, Inc.

(57) ABSTRACT

An absorbent article (10) can include a pocket (64) disposed in the front waist region 12. The pocket (64) can include a first side edge (70), a second side edge (72), an upper lateral edge (74), and a lower lateral edge (76). The pocket (64) can be closed with respect to the absorbent assembly (44) at least at the first side edge (70) and the second side edge (72) and can be open with respect to the absorbent assembly (44) at least at the lower lateral edge (76). In one embodiment, at least a portion of the upper lateral edge (74) can be closer to the front waist edge (22) of the absorbent article (10) than is the first end edge (40) of the absorbent body (34).

19 Claims, 6 Drawing Sheets

(51) Int. Cl.
  *A61F 13/551* (2006.01)
  *A61F 13/56* (2006.01)
  *A61F 13/514* (2006.01)

(52) U.S. Cl.
  CPC . *A61F 13/5622* (2013.01); *A61F 2013/49092* (2013.01); *A61F 2013/55125* (2013.01); *A61F 2013/5683* (2013.01)

(58) Field of Classification Search
  CPC .. A61F 2013/49098; A61F 2013/49493; A61F 2013/55125; A61F 2013/5683; A61F 2013/8402
  See application file for complete search history.

(56) References Cited

U.S. PATENT DOCUMENTS

| | | | |
|---|---|---|---|
| 5,593,401 A * | 1/1997 | Sosalla | A61F 13/49011 604/385.28 |
| 5,904,675 A * | 5/1999 | Laux | A61F 13/49009 604/385.29 |
| 5,938,652 A | 8/1999 | Sauer | |
| 6,258,076 B1 | 7/2001 | Glaug et al. | |
| 6,264,639 B1 | 7/2001 | Sauer | |
| 6,425,889 B1 | 7/2002 | Kitaoka et al. | |
| 6,485,478 B2 | 11/2002 | Imai et al. | |
| 7,294,121 B2 * | 11/2007 | Kawata | A61F 13/4704 604/385.13 |
| 7,727,211 B2 | 6/2010 | Beck | |
| 7,982,090 B2 | 7/2011 | Snauwaert et al. | |
| 7,993,314 B2 | 8/2011 | Asp et al. | |
| 2001/0037102 A1 | 11/2001 | Sugito | |
| 2003/0109841 A1 | 6/2003 | Edwards | |
| 2005/0137564 A1 | 6/2005 | Strannemalm | |
| 2005/0143710 A1 | 6/2005 | Van Gompel et al. | |
| 2006/0111685 A1 | 5/2006 | Kawata et al. | |
| 2006/0241558 A1 | 10/2006 | Ramshak | |
| 2006/0282056 A1 | 12/2006 | McDonald | |
| 2007/0032769 A1 | 2/2007 | Cohen et al. | |
| 2008/0051744 A1 | 2/2008 | Cummings | |
| 2011/0034896 A1 | 2/2011 | Bai | |
| 2011/0092939 A1 | 4/2011 | Donoho | |
| 2012/0071850 A1 | 3/2012 | Tomassetti | |

FOREIGN PATENT DOCUMENTS

| | | |
|---|---|---|
| GB | 2 326 811 A | 1/1999 |
| GB | 2 389 300 A | 12/2003 |
| WO | WO 1998/013002 A1 | 4/1998 |

* cited by examiner

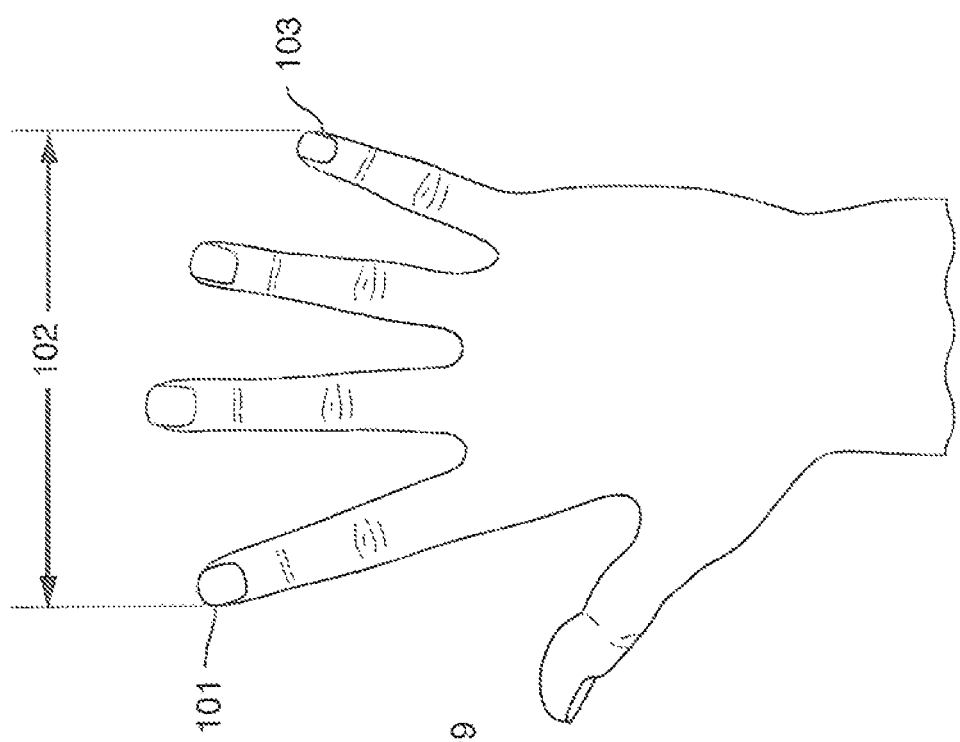
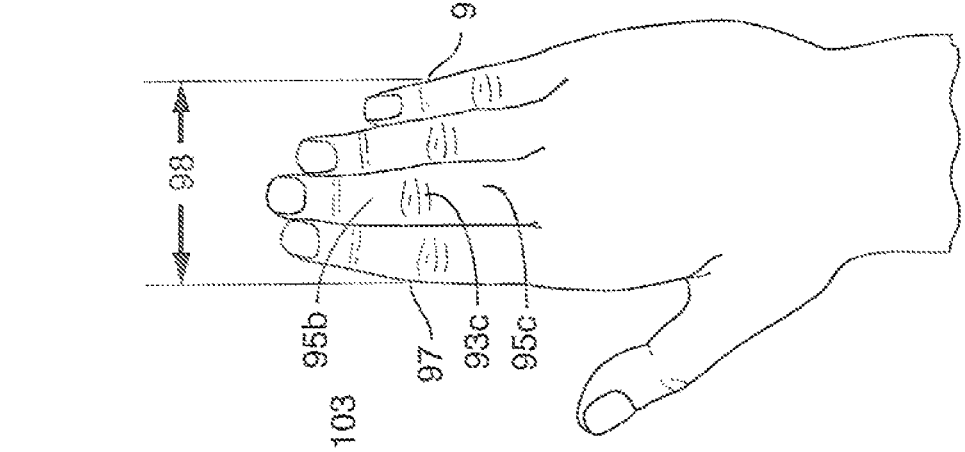
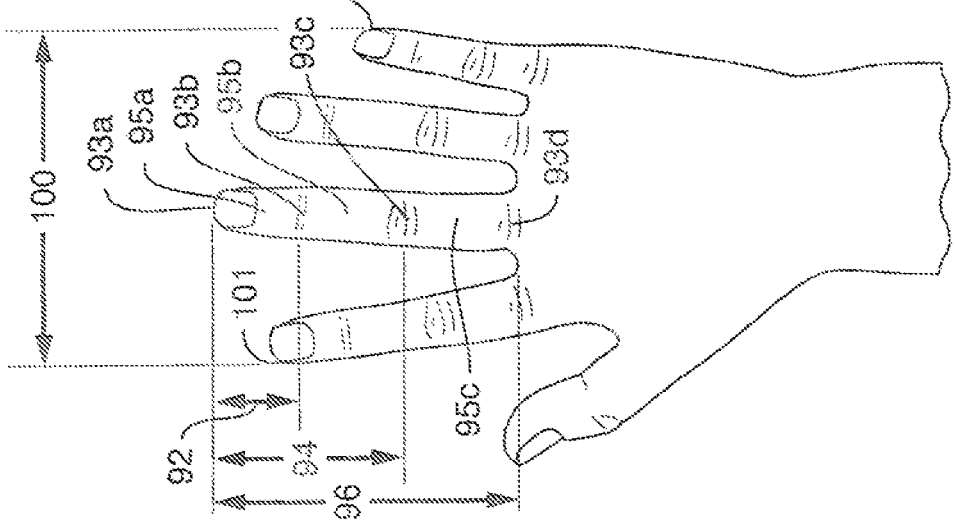

ABSORBENT ARTICLE WITH POCKET PROVIDING ENHANCED CONTROL

TECHNICAL FIELD

The present invention relates to absorbent articles.

BACKGROUND OF THE DISCLOSURE

When absorbent articles become soiled with exudates and are changed from the wearer, it is common for the lower abdomen and/or crotch region of the wearer to become soiled by urine, fecal matter, and/or other bodily discharges. Prior to replacing the soiled absorbent article and replacing it with a new, clean absorbent article, the skin of the wearer is cleansed. This cleaning of the skin can be done in a variety of ways and using a variety of different materials, but caregivers commonly use wet wipes or cloths to clean the wearer's skin. In some circumstances, caregivers may choose to use a clean portion of an inner layer of the soiled absorbent article to provide a first wipe to cleanse the wearer's skin in the lower abdomen or crotch region prior to using wet wipes, cloths, or tissues.

To perform this initial wipe, a caregiver may attempt to pinch or gather the front waist region of the absorbent article to obtain a grip on the absorbent article to use the inner layer of the absorbent article in a wiping fashion. However, pinching or gathering the front waist region of the absorbent article can reduce the effective area of the inner layer of the absorbent article that is intended to wipe the wearer's skin in the soiled area as well as create an uneven inner surface of the absorbent article that is not as conducive to wiping as the initial flat surface. Pinching or gathering the front waist region of the absorbent article in this fashion may also expose a caregiver's fingers or hand to the exudates remaining on the wearer's skin, as the gathered material in the front waist region may fold over due to pinching or gathering of the absorbent article near the front waist edge of the absorbent article where the absorbent article may have less structural integrity and/or due to the wiping motion of the caregiver employs with the absorbent article. Additionally, gripping the front waist region of the absorbent article in such a fashion may prove to be difficult altogether as the outer cover materials may have a low coefficient of friction, resulting in the gathered or pinched area of the front waist region slipping out of the caregiver's hands while trying to wipe the soiled area. While some of these issues have been recognized in prior documents, no effective solution has been provided to date to adequately address these issues.

Thus, there remains a need for an absorbent article that can provide improved functionality for the caregiver to utilize the absorbent article as a first wipe to cleanse the wearer's skin. There also remains a need for an absorbent article that protects the caregiver's hands from the wearer's exudates while still providing a proper grip on the absorbent article to utilize the absorbent article in a wiping fashion.

SUMMARY OF THE DISCLOSURE

In one embodiment, an absorbent article can include a front waist region including a front waist edge, a rear waist region including a rear waist edge, and a crotch region. The absorbent article can further include a longitudinal axis and a lateral axis. The absorbent article can also include an absorbent assembly including a bodyside liner, an outer cover, and an absorbent body disposed between the bodyside liner and the outer cover. The absorbent body can include a first longitudinal edge, a second longitudinal edge opposite from the first longitudinal edge, a first end edge, and a second end edge. The first end edge can be disposed in the front waist region. The absorbent article can also include a pocket disposed in the front waist region. The pocket can include a first side edge, a second side edge opposite from the first side edge, an upper lateral edge, and a lower lateral edge. At least a portion of the upper lateral edge of the pocket can be closer to the front waist edge than is the first end edge of the absorbent body. The pocket can be closed with respect to the absorbent assembly at the first side edge, the second side edge, and the upper lateral edge and can be open with respect to the absorbent assembly at the lower lateral edge.

In another embodiment, an absorbent article can include a front waist region including a front waist edge, a rear waist region including a rear waist edge, and a crotch region. The absorbent article can further include a longitudinal axis and a lateral axis. The absorbent article can also include an absorbent assembly including a bodyside liner, an outer cover, and an absorbent body disposed between the bodyside liner and the outer cover. The absorbent body can include a first longitudinal edge, a second longitudinal edge opposite from the first longitudinal edge, a first end edge, and a second end edge. The first end edge can be disposed in the front waist region. The absorbent article can also include a pocket disposed in the front waist region. The pocket can have a pocket longitudinal axis that is substantially aligned with the longitudinal axis of the absorbent article. The pocket can include a first side edge, a second side edge opposite from the first side edge, an upper lateral edge, and a lower lateral edge. The pocket can be closed with respect to the absorbent assembly at the first side edge, the second side edge, and the upper lateral edge. The pocket can be open with respect to the absorbent assembly at the lower lateral edge. The pocket can have a width defined between the first side edge and the second side edge and can have a length defined between the upper lateral edge and the lower lateral edge. The width can be between about 3.00 inches and about 6.00 inches. The length can be between about 1.25 inches and about 3.75 inches.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 3a is a top plan view of an exemplary hand in a relaxed position.

FIG. 3b is a top plan view of the hand of FIG. 3a in a closed finger position.

FIG. 3c is a top plan view of the hand of FIG. 3a in an extended finger position.

Figure 1:
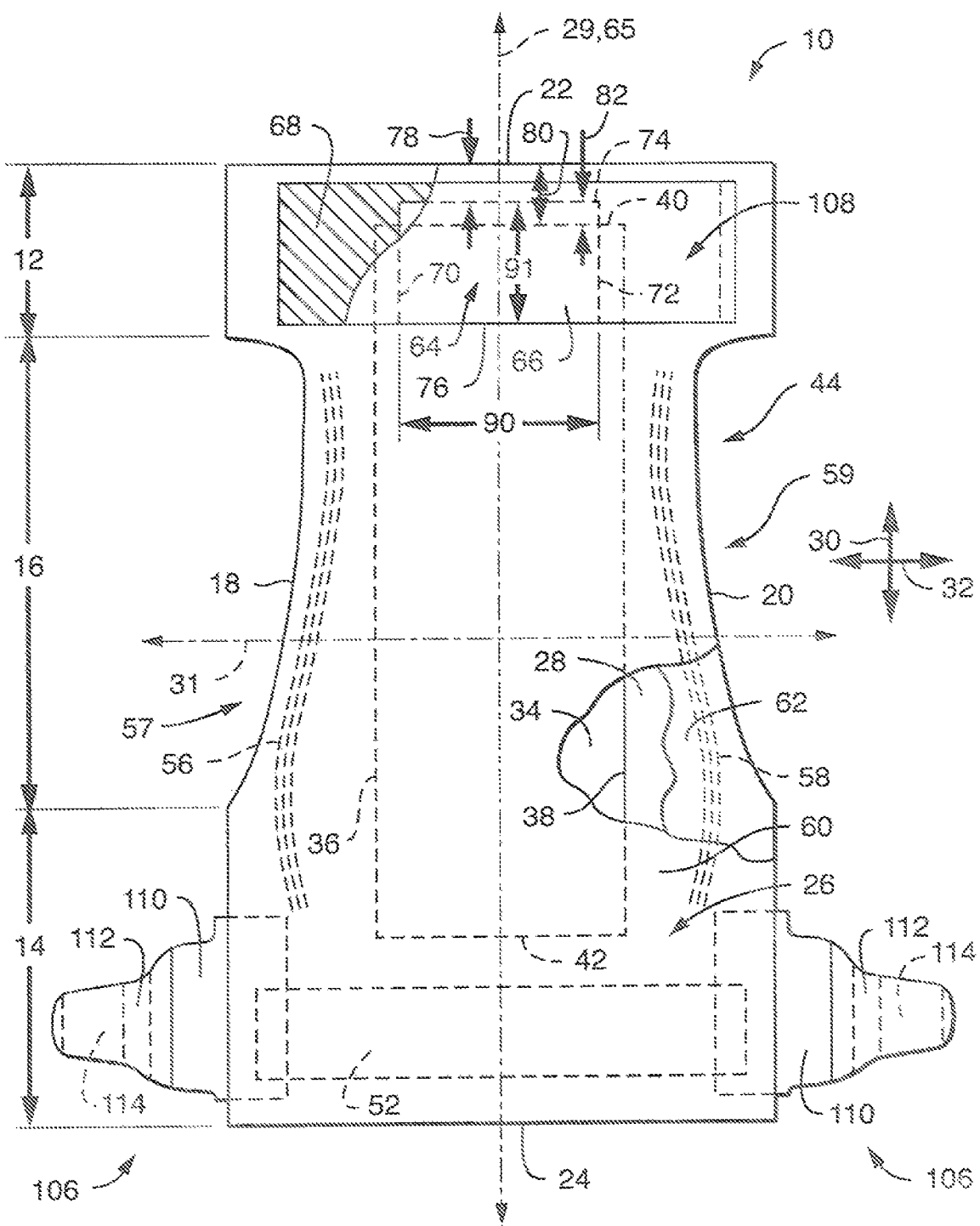
FIG. 1 is a top plan view of an exemplary embodiment of an absorbent article including a pocket, the absorbent article being in a stretched, laid flat configuration, with the outer cover facing the viewer.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having a pocket disposed on the outer surface in the front waist region of the absorbent article. The pocket can aid a caregiver with providing an initial cleaning of the wearer after the article is soiled by the wearer and prior to changing the absorbent article. In preferred embodiments, the selective location and size of the pocket can provide advantages to the caregiver, which are discussed further below. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, training pant, youth pant, incontinent product, or other absorbent article about the wearer of one of these absorbent articles. A user and a wearer can be one and the same person.

Figure 2:
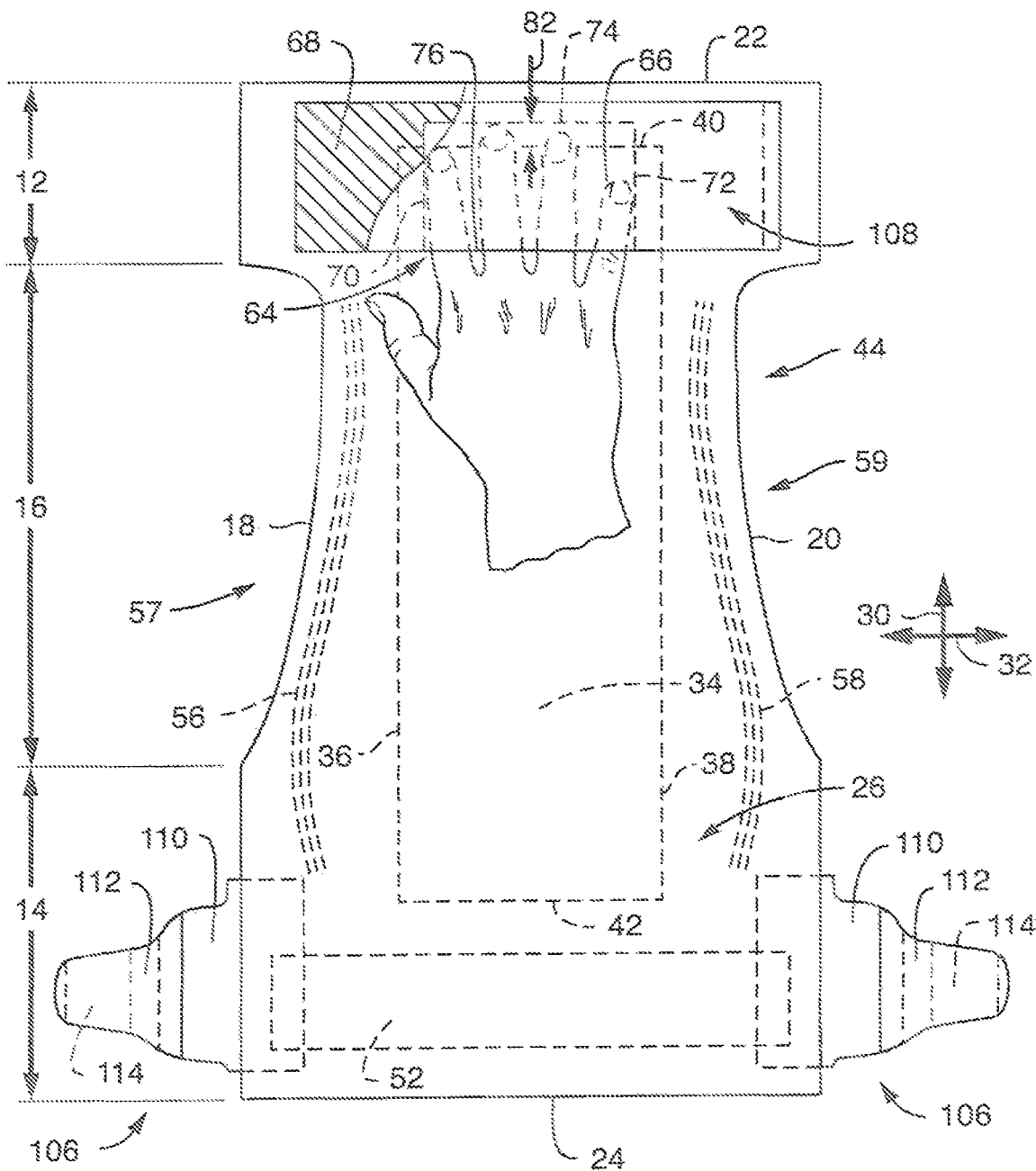
FIG. 2 is a top plan view of the absorbent article of FIG. 1 illustrating a caregiver's fingers in the pocket.

Absorbent Article:

Referring to FIGS. 1 and 2, a non-limiting illustration of an absorbent article 10, for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIGS. 1 and 2 includes a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. The absorbent article 10 has a pair of longitudinal side edges, 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define a central waist opening for the waist of the wearer. Portions of the longitudinal side edges, 18 and 20, in the crotch region 16 can generally define leg openings for the legs of the wearer when the absorbent article 10 is worn.

The absorbent article 10 can include an outer cover 26 and a bodyside liner 28, the bodyside liner 28 being depicted in the cut-away portion of FIG. 1. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIG. 1, the absorbent article 10 can have a longitudinal axis 29 extending in the longitudinal direction 30 and a lateral axis 31 extending in the lateral direction 32.

An absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10. The absorbent body 34 can have opposite first and second end edges, 40 and 42, respectively, which, in an embodiment, can form portions of the waist edges, 22 and 24, respectively, of the absorbent article 10. The first end edge 40 can be in the front waist region 12. The second end edge 42 can be in the rear waist region 14. In an embodiment, the absorbent body 34 can have a length and width that are the same as or less than the length and width of the absorbent article 10. The bodyside liner 28, the outer cover 26, and the absorbent body 34 can form part of an absorbent assembly 44. The absorbent assembly 44 can also include other components not shown herein, such as a fluid transfer layer and a fluid acquisition layer, as are known in the art.

The absorbent article 10 can be configured to contain and/or absorb liquid, solid, and semi-solid body exudates discharged from the wearer. For example, containment flaps (not shown), which are known in the art, can be configured to provide a barrier to the lateral flow of body exudates. To further enhance containment and/or absorption of body exudates, in some embodiments the absorbent article 10 can suitably include a waist elastic member, such as a rear waist elastic member 52. In some embodiments, the absorbent article 10 can include a front waist elastic member, although one is not depicted herein. The absorbent article 10 can further include leg elastic members, 56 and 58, as are known to those skilled in the art. The rear waist elastic member 52 can be attached to the outer cover 26 and/or the bodyside liner 28 along the rear waist edge 24 and can extend over part or all of the rear waist edge 24. In an embodiment shown in FIGS. 1 and 2, the rear waist elastic member 52 is attached to the bodyside liner 28. The leg elastic members, 56 and 58, can be attached to the outer cover 26 and/or the bodyside liner 28 along the opposite longitudinal side edges, 18 and 20, and positioned in the crotch region 16 of the absorbent article 10. The leg elastic members, 56 and 58, can be curved as shown in FIGS. 1 and 2, or can be parallel to the longitudinal axis 29 as is known in the art.

Additional details regarding each of these elements of the absorbent article 10 described herein can be found below and with reference to the FIGS. 1 through 8.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In an embodiment, such as that shown in FIGS. 1 and 2, the outer cover 26 can be a two layer construction, including an outer layer 60 material and an inner layer 62 material which can be bonded together such as by a laminate adhesive. Suitable laminate adhesives can be applied continuously or intermittently as beads, a spray, parallel swirls, or the like, but it is to be understood that the inner layer 62 can be bonded to the outer layer 60 by other bonding methods, including, but not limited to, ultrasonic bonds, thermal bonds, pressure bonds, or the like.

The outer layer 60 of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 60 of an outer cover 26 can be a 20 gsm spunbond polypropylene non-woven web. The outer layer 60 may also be constructed of the same materials from which the bodyside liner 28 can be constructed as described herein.

The liquid impermeable inner layer 62 of the outer cover 26 (or the liquid impermeable outer cover 26 where the outer cover 26 is of a single-layer construction) can be either vapor permeable (i.e., "breathable") or vapor impermeable. The liquid impermeable inner layer 62 (or the liquid impermeable outer cover 26 where the outer cover 26 is of a single-layer construction) can be manufactured from a thin plastic film. The liquid impermeable inner layer 62 (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

Where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

As shown in FIGS. 1 and 2, a pocket 64 can be disposed in the front waist region 12 of the absorbent article 10. The pocket 64 can include a pocket longitudinal axis 65, as shown in FIG. 1. Preferably, the pocket longitudinal axis 65 substantially aligns with the longitudinal axis 29 of the absorbent article 10. In some embodiments, the pocket 64 can be formed from a pocket material 66 coupled to the outer cover 26. The pocket material 66 can be coupled to the outer cover 26 by any suitable method known in the art, such as by adhesive 68, as shown in the embodiment of the absorbent article in FIGS. 1 and 2.

The pocket 64 can include a first side edge 70 and a second side edge 72. The second side edge 72 can be opposite from the first side edge 70. The pocket 64 can also include an upper lateral edge 74 and a lower lateral edge 76. The pocket 64 can be closed with respect to the absorbent assembly 44 at the first side edge 70, the second side edge 72, and the upper lateral edge 74. As shown in the embodiment depicted in FIGS. 1 and 2, the pocket 64 is closed with respect to the absorbent assembly 44 in this manner due to the selective location of the adhesive 68. The pocket 64 can be open with respect to the absorbent assembly 44 at the lower lateral edge 76. The open nature of the pocket 64 at the lower lateral edge 76 allows a caregiver's hand, such as shown in FIG. 2, to enter the pocket 64 to assist with an initial wiping of the skin of the wearer after the article 10 becomes soiled with exudates prior to disposing of the soiled absorbent article 10 and cleansing the wearer's skin, as will be discussed in further detail below. In some embodiments, the pocket 64 can be open with respect to absorbent assembly 44 at the upper lateral edge 74 as well as at the lower lateral edge 76.

The pocket 64 can be disposed in the front waist region 12 of the absorbent article 10 with particular positioning with respect to the absorbent body 34 to provide an enhanced ability for the caregiver to maintain their hand in the pocket 64 and maintain their grip during wiping of a wearer of the absorbent article 10. In one respect, the pocket 64 can be disposed in the front waist region 12 such that at least a portion of the upper lateral edge 74 of the pocket 64 is closer to the front waist edge 22 of the absorbent article 10 than is the first end edge 40 of the absorbent body 34. Stated in other words and referring to FIG. 1, a distance 78 between the upper lateral edge 74 of the pocket 64 and the front waist edge 22 of the absorbent article 10 is less than a distance 80 between the first end edge 40 of the absorbent body 34 and the front waist edge 22 of the absorbent article 10, where the distances 78, 80 are measured in a direction parallel to the longitudinal axis 29 of the absorbent article and at a substantially similar lateral location of the absorbent article 10 (distances 78, 80 being shown in FIG. 1 at different lateral locations for purposes of clarity).

Configuring the pocket 64 such that at least a portion of the upper lateral edge 74 is closer to the front waist edge 22 than is the first end edge 40 of the absorbent body 34 provides a distance 82 between the upper lateral edge 74 of the pocket 64 and the first end edge 40 of the absorbent body 34. This distance 82 can provide room for one or more of a caregiver's fingers to rest against the first end edge 40 of the absorbent body 34 when the caregiver's fingers are inserted into the pocket 64 and provides an improved grip of the pocket 64 and the absorbent article 10. In preferred embodiments, the distance 82 between the at least a portion of the upper lateral edge 74 of the pocket 64 and the first end edge 40 of the absorbent body 34 is greater than about 0.25 inches, and more preferably greater than about 0.50 inches. In a preferred embodiment, the distance 82 between the at least a portion of the upper lateral edge 74 of the pocket 64 and the first end edge 40 of the absorbent body 34 is between about 0.25 inches and about 0.75 inches. As shown in FIG. 2, in such preferred embodiments, one or more of the user's fingers placed inside of the pocket 64 can rest in the region of distance 82 and can experience enhanced control of the pocket 64 by pressing against the upper lateral edge 74 of the pocket 64 while at the same time pressing against the first end edge 40 of the absorbent body 34. Of course, it is contemplated that embodiments can be configured with ranges of distance 82 outside of this preferred range, yet still provide some advantages of enhanced control of the pocket 64.

The pocket 64 can also be constructed to provide similar enhanced control by its relative positioning to one or more longitudinal edges 36, 38 of the absorbent body 34. For example, in the embodiment depicted in FIG. 4, at least a portion of the first side edge 70 of the pocket 64 can be closer to the first longitudinal side edge 18 of the absorbent article 10 than is the first longitudinal edge 36 of the absorbent body 34. Stated in other words, a distance 84 between the first side edge 70 of the pocket 64 and the first longitudinal side edge 18 of the absorbent article 10 is less than a distance 85 between the first longitudinal edge 36 of the absorbent body 34 and the first longitudinal side edge 18 of the absorbent article 10, where the distances 84, 85 are measured in a direction parallel to the lateral axis 31 and at a substantially similar longitudinal location of the absorbent article 10. Such a configuration provides the pocket 64 such that there is a distance 88 between the first side edge 70 of the pocket 64 and the first longitudinal edge 36 of the absorbent body 34 where the first side edge 70 of the pocket 64 is laterally outside of the first longitudinal edge 36 of the absorbent body 34.

Similarly, at least a portion of the second side edge 72 of the pocket 64 can be closer to the second longitudinal side edge 20 of the absorbent article 10 than is the second longitudinal edge 38 of the absorbent body 34. Stated in other words, a distance 86 between the second side edge 72 of the pocket 64 and the second longitudinal side edge 20 of the absorbent article 10 is less than a distance 87 between the second longitudinal edge 38 of the absorbent body 34 and the second longitudinal side edge 20 of the absorbent article 10, where the distances 86, 87 are measured in a direction parallel to the lateral axis 31 and at a substantially similar longitudinal location of the absorbent article 10. Such a configuration provides the pocket 64 with a distance 89 between the second side edge 72 of the pocket 64 and the second longitudinal edge 38 of the absorbent body 34 where the second side edge 72 of the pocket 64 is laterally outside of the second longitudinal edge 38 of the absorbent body 34.

Figure 4:
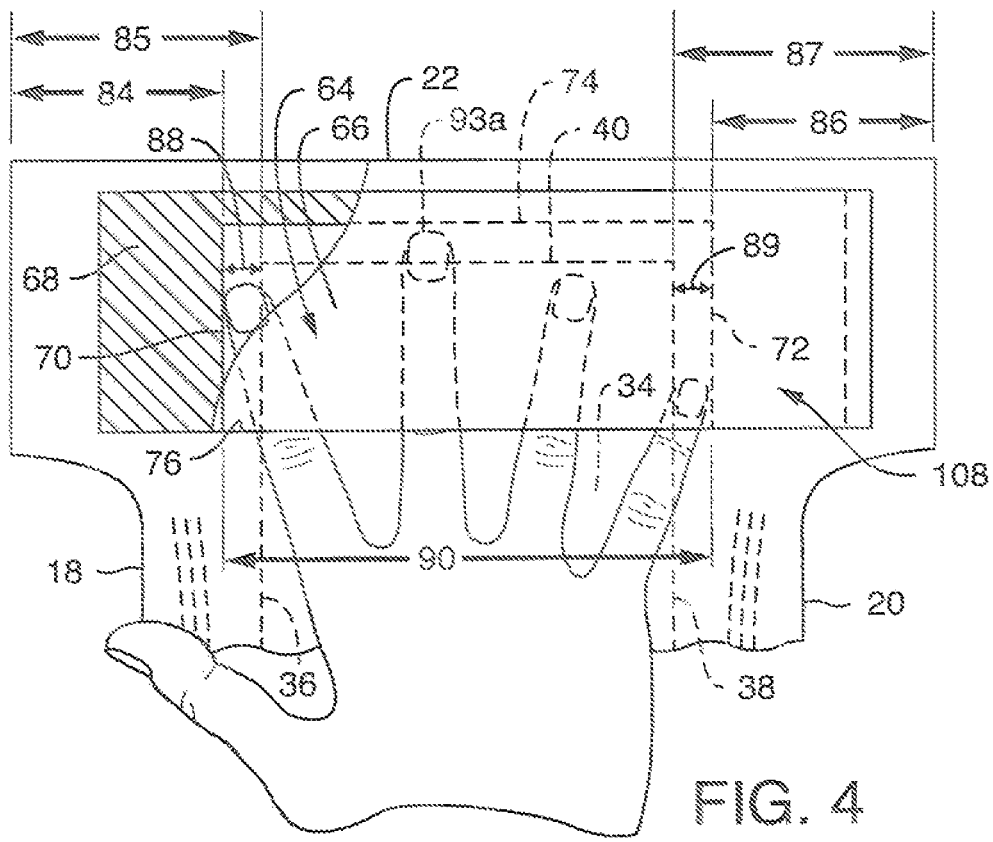
FIG. 4 is a detailed view of an alternative embodiment of an absorbent article and depicting an exemplary hand in an extended finger position with the fingers in the pocket of the absorbent article.

Similar to the discussion above with distance 82 between the upper lateral edge 74 of the pocket 64 and the first end edge 40 of the absorbent body 34, distances 88, 89 between the first side edge 70 of the pocket 64 and the first longitudinal edge 36 of the absorbent body 34 and between the second side edge 72 of the pocket 64 and the second longitudinal edge 38 of the absorbent body 34, respectively, can provide enhanced control of the pocket 64 by providing space for a user's finger tips to rest against the longitudinal edges 36, 38 of the absorbent body 34, such as shown in FIG. 4. In preferred embodiments, distances 88, 89 can be greater than about 0.25 inches, and more preferably greater than about 0.50 inches. In some embodiments, distances 88, 89 can be between about 0.25 inches and about 0.75 inches. It is to be noted that a pocket 64 can be configured with one or more features provided by distances 82, 88, and/or 89 discussed above, or all of the features provided by distances 82, 88, and 89. However, an embodiment including only one of the features provided by distances 82, 88, and 89 can still provide the advantage of enhanced control of the pocket 64 in a wiping action on the wearer's skin.

The pocket 64 can also be selectively designed to have width 90 and length 91 configurations that provide enhanced handling and control of the pocket 64 when wiping the wearer of the absorbent article 10. As used herein, the length 91 of the pocket 64 is measured between the upper lateral edge 74 of the pocket 64 to the lower lateral edge 76 of the pocket 64 in a direction parallel to the longitudinal axis 29 of the absorbent article 10. As used herein, the width 90 of the pocket 64 is measured between the first side edge 70 of the pocket 64 and the second side edge 72 of the pocket 64 in a direction parallel to the lateral axis 31 of the absorbent article 10.

As depicted in FIG. 3a, in analyzing consumer anthropometric data, it was determined that an average distance 92 between the tip 93a of the second finger of a female's hand and the first finger joint 93b between the distal phalanx 95a and the middle phalanx 95b is about 1.25 inches. Further, analysis of consumer anthropometric data provided that the average distance 94 between the tip 93a of the second finger of a female's hand and the second finger joint 93c between the middle phalanx 95b and the proximal phalanx 95c is about 2.50 inches, and the average distance 96 between the tip 93a of the second finger of a female's hand and the second finger metacarpophalangeal joint 93d is about 3.75 inches.

In view of this anthropometric data and confidential consumer feedback, it was found that a pocket 64 with a length 91 that is less than the average distance 92 between the tip 93*a* of the second finger of a female's hand and the first finger joint 93*b* between the distal phalanx 95*a* and the middle phalanx 95*b* (about 1.25 inches), while saving on material cost, provides less than desirable finger coverage and control of the pocket 64 during wiping of the wearer. Thus, as shown in FIG. 6*b*, a minimum to the preferable range of the length 91 of the pocket 64 is about 1.25 inches, such that the pocket material 66 can extend from the tip 93*a* of the caregiver's second finger to the first finger joint 93*b* between the distal phalanx 95*a* and the middle phalanx 95*b*.

Additionally, analysis of confidential consumer feedback provided that a pocket 64 with a length 91 that is greater than the average distance 96 between the tip 93*a* of the second finger of a female's hand and the second finger metacarpophalangeal joint 93*d* provided greater finger coverage, however, created difficulty for caregivers to insert their fingers into the pocket 64. Additionally, the increased length 91 of the pocket 64 created additional cost in pocket material 66. Thus, as shown in FIG. 6*c*, a maximum to the preferable range of the length 91 of the pocket 64 is about 3.75 inches. Such a result was unexpected in that it was initially thought that having a pocket of greater length would provide more grip against the user's hand and would be preferred.

Figure 6A:
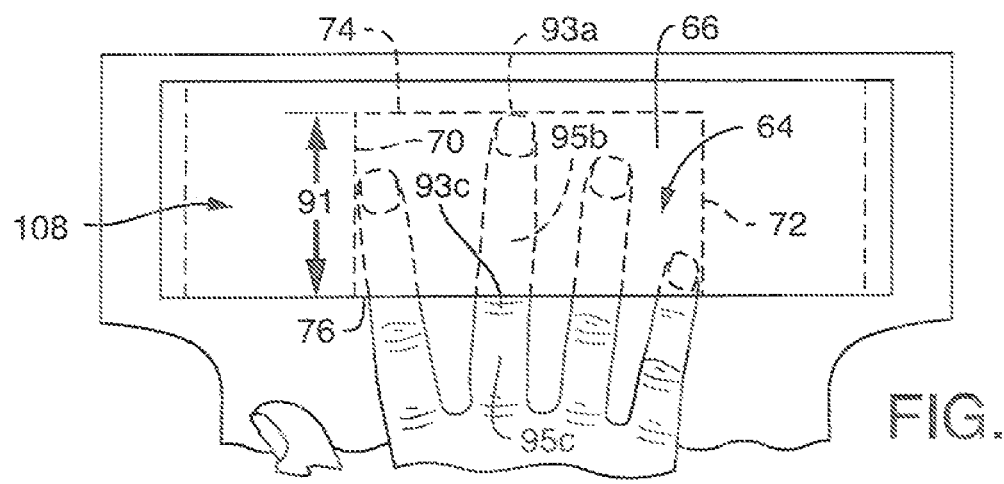
FIG. 6a is detailed view of another alternative embodiment of an absorbent article and depicting an exemplary hand in a relaxed position with the fingers in the pocket.
Figure 6B:
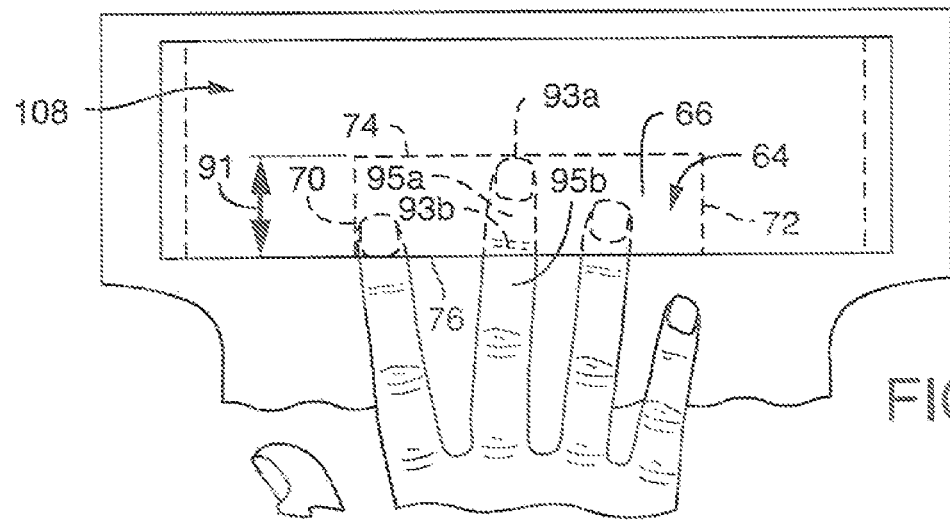
FIG. 6b is a detailed view of still another alternative embodiment of an absorbent article and depicting an exemplary hand in a relaxed position with the fingers in the pocket.
Figure 6C:
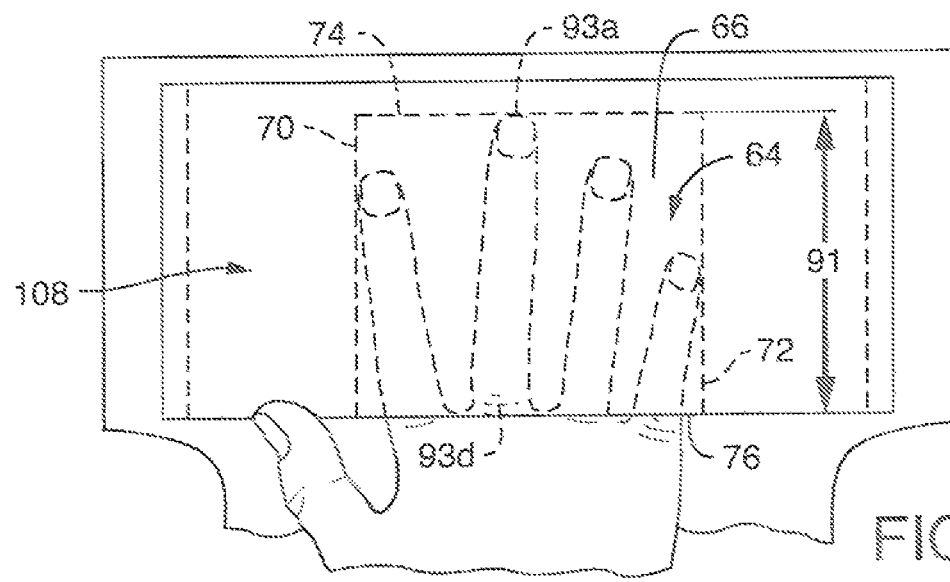
FIG. 6c is a detailed view of another alternative embodiment of an absorbent article and depicting an exemplary hand in a relaxed position with the fingers in the pocket.

FIG. 6*a* provides a preferred embodiment of a pocket 64 with a length 91 of about 2.50 inches. In FIG. 6*a*, the length 91 of the pocket 64 is equal to the average distance 94 between the tip 93*a* of the second finger of a female's hand and the second finger joint 93*c* between the middle phalanx 95*b* and the proximal phalanx 95*c*, which is about 2.50 inches. A length 91 of about 2.50 inches provides the advantage of having adequate finger coverage to protect the caregiver's hand while employing the pocket 64 to use the absorbent article 10 to initially wipe the wearer's skin after the absorbent article 10 becomes soiled. Additionally, having a length 91 of about 2.50 inches still provides adequate control of the pocket 64 during wiping. Such a length 91 of about 2.50 inches was also beneficial for providing eased insertion of a caregiver's fingers into the pocket 64 as compared to pockets 64 having larger lengths 91.

Referring back to FIG. 3*b*, in analyzing the consumer anthropometric data, it was determined that an average distance 98 between the inside edge 97 of a first finger of a female's hand at approximately the longitudinal length that aligns with the second finger joint 93*c* between the middle phalanx 95*b* and the proximal phalanx 95*c* of the second finger and the outside of the hand 99 as measured laterally is about 3.00 inches when the hand is in a closed finger position. When the fingers are in a relaxed position, such as shown in FIG. 3*a*, consumer anthropometric data provided that the average distance 100 between the outer edge 101 of the first finger and the outer edge 103 of the fourth finger is about 4.00 inches. When the hand is in the extended finger position, such as shown in FIG. 3*c*, consumer anthropometric data provided that the average distance 102 between the outer edge 101 of the first finger and the outer edge 103 of the fourth finger is about 6.00 inches.

Figure 5:
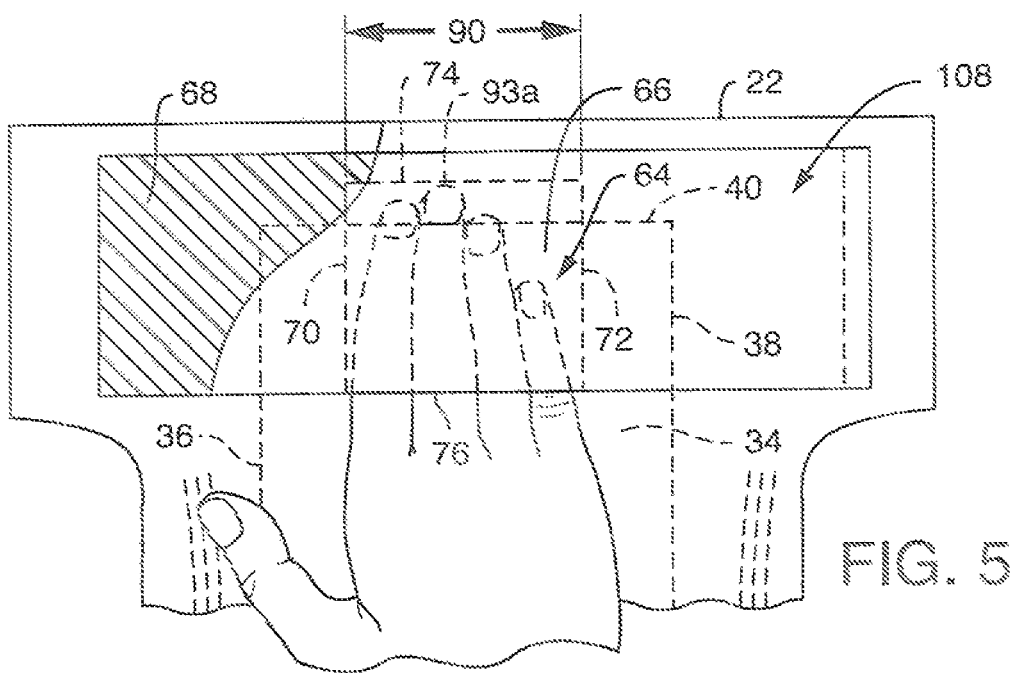
FIG. 5 is a detailed view of yet another alternative embodiment of an absorbent article and depicting an exemplary hand in a closed finger position with the fingers in the pocket.

From analysis of the anthropometric data and review of confidential consumer feedback, a pocket 64 including a width 90 that is less than about 3.00 inches can provide difficulty for some caregivers to insert their fingers into the pocket 64 to a sufficient length to adequately control the pocket 64. Thus, as shown in FIG. 5, a minimum preferred width 90 for the pocket 64 is about 3.00 inches. Conversely, a pocket 64 having a width 90 that is greater than about 6.00 inches can provide difficulty for a caregiver to expand their hand and apply a force to the first and second side edges 70, 72 of the pocket 64 to maintain control of the pocket 64 while wiping the wearer's skin. As shown in FIG. 4, a maximum preferred width 90 of the pocket 64 is about 6.00 inches.

FIG. 2 displays a preferred embodiment of a pocket 64 having a width 90 of about 4.00 inches. Such a configuration provides for the average distance 100 between the outer edge 101 of the first finger and the outer edge 103 of the fourth finger when the caregiver's hand is in a relaxed position. A width of about 4.00 inches provides enough space for the caregiver to slide their fingers into the pocket 64 comfortably while requiring minimal finger expansion in the lateral direction 32 to apply force against the first and second side edges 70, 72 of the pocket 64 during wiping of the wearer of the absorbent article 10. Applying force against the side edges 70, 72 of the pocket 64 increases control of the pocket 64 and of the absorbent article 10 during cleaning of the wearer's skin.

Thus, using the consumer anthropometric data of an average female hand in view of learnings from confidential consumer data, the length 91 of the pocket 64 is preferably configured to be between about 1.25 inches and about 3.75 inches, and more preferably between about 2.00 inches and about 3.00 inches. In a preferred embodiment, the length 91 of the pocket 64 can be about 2.50 inches. Furthermore, the width 90 of the pocket 64 is preferably configured to be between about 3.00 inches and about 6.00 inches, and more preferably between about 3.50 inches and about 4.50 inches. In a preferred embodiment, the width 90 of the pocket 64 is about 4.00 inches.

The pocket 64 can be designed to be of various shapes. For example, in the embodiment shown in FIGS. 1, 2, and 4-6*c*, the pocket 64 can be generally rectangular in shape with the first side edge 70 being parallel to the second side edge 72 and the upper lateral edge 74 being parallel to the lower lateral edge 76. The upper and lower lateral edges 74, 76, respectively, can be parallel to the lateral axis 31 of the absorbent article 10. In such an embodiment where the first end edge 40 of the absorbent body 34 is parallel to the lateral axis 31 as well, the distance 82 between the at least a portion of the upper lateral edge 74 of the pocket 64 and the first end edge 40 of the absorbent body 34 is substantially consistent along the entire length of the upper lateral edge 74 of the pocket 64. Thus, the benefits noted above with respect to the distance 82 between the at least a portion of the upper lateral edge 74 of the pocket 64 and the first end edge 40 of the absorbent body 34 providing enhanced control of the pocket 64 can be used along a substantial width of the pocket 64 along the upper lateral edge 74 of the pocket 64.

Figure 7:
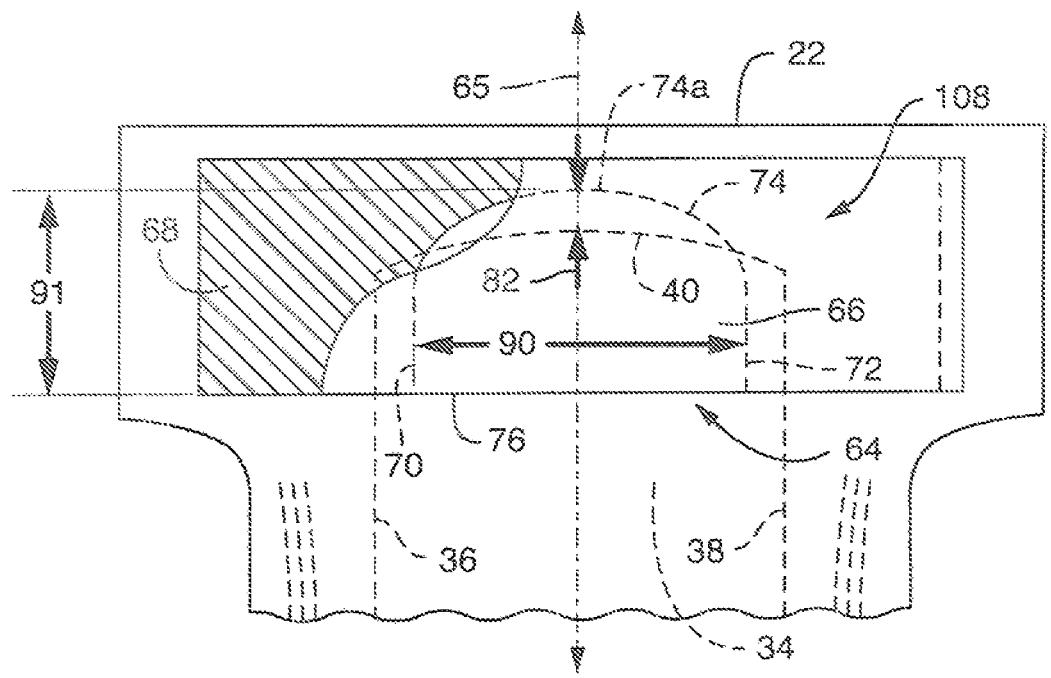
FIG. 7 is a detailed view of another alternative embodiment of an absorbent article including a pocket, the pocket having a curved upper lateral edge.

In some embodiments, however, such as shown in FIG. 7, the upper lateral edge 74 of the pocket 64 can be curved. In the embodiment shown in FIG. 7, the upper lateral edge 74 can be convex with respect to the front waist edge 22 of the absorbent article 10. In the embodiment illustrated in FIG. 7, the curved shape of the upper lateral edge 74 still provides at least a portion 74*a* of the upper lateral edge 74 that is closer to the front waist edge 22 than is the first end edge 40 of the absorbent body 34. Specifically, a portion 74*a* of the upper lateral edge 74 in the pocket 64 illustrated in FIG. 7 is closer to the front waist edge 22 than is the first end edge 40 of the absorbent body 34. Such a curved configuration of the upper lateral edge 74 may also more closely match how a caregiver's fingertips are spread out in the pocket 64 when the caregiver's fingers are spread in a relaxed hand position. If only a portion 74*a* of the upper lateral edge 74 is closer to the front waist edge 22 than is the first end edge 40 of the absorbent body 34, then preferably the portion 74a of the upper lateral edge 74 is configured such that at least some of the portion 74a is near the longitudinal axis 65 of the pocket 64. Such a configuration can provide a distance 82 between the portion 74a of the upper lateral edge 74 of the pocket 64 and the first end edge 40 of the absorbent body 34 to provide space for at least the caregiver's third and/or fourth fingers to be placed when wiping and provide enhanced control of the pocket 64.

Figure 8:
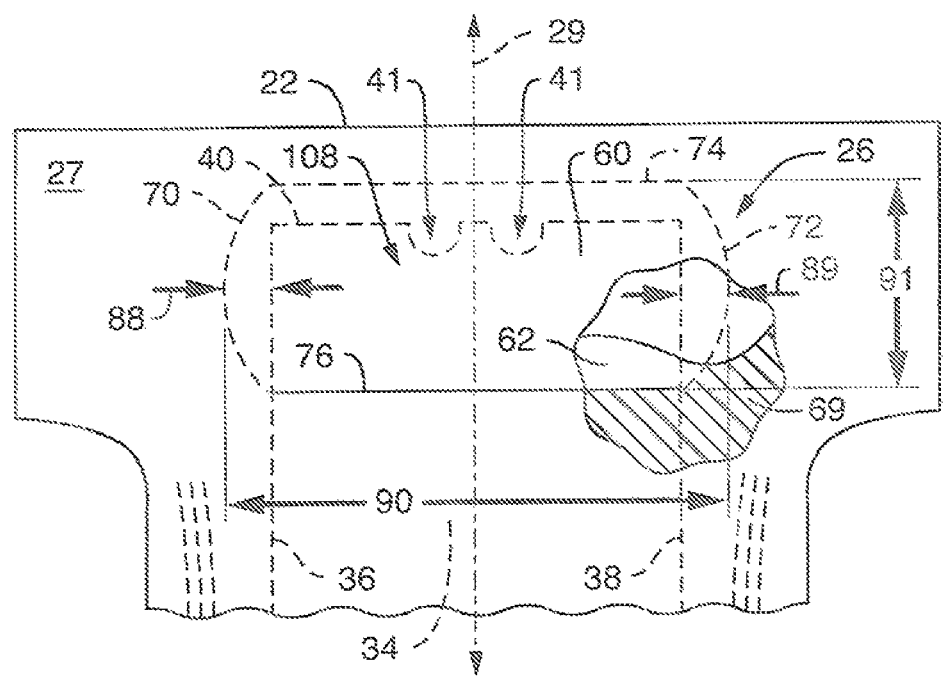
FIG. 8 is a detailed view of another alternative embodiment of an absorbent article including a pocket, the pocket being formed between two layers of the outer cover.

In some embodiments, such as shown in FIG. 8, the first side edge 70 and the second side edge 72 of the pocket 64 can each be curved. In the embodiment shown in FIG. 8, the first side edge 70 and the second side edge 72 can each be curved such that they are concave with respect to the longitudinal axis 29 of the absorbent article 10. Thus, the pocket 64 can provide a distance 88 between the first side edge 70 of the pocket 64 and the first longitudinal edge 36 of the absorbent body 34 as well as a distance 89 between the second side edge 72 of the pocket 64 and the second longitudinal edge 38 of the absorbent body 34 to provide space for one or more fingers of a caregiver's hand to be placed on each side of the pocket 64 when wiping and provide enhanced control of the pocket 64. Of course, it is contemplated that the pocket 64 can be of other shapes as well.

Although the pocket 64 can be formed with pocket material 66 that is coupled to the outer cover 26 of the absorbent article 10 such as with adhesive 68 (as shown in FIGS. 1, 2, and 4-7), the pocket 64 can be formed in other ways and is not limited to such a configuration. For example, FIG. 8 depicts a pocket 64 that is formed between two layers 60, 62 of the outer cover 26. The pocket 64 is formed where the outer layer 60 is not adhered to the inner layer 62 with adhesive 69. The lower lateral edge 76 of the pocket 64 is formed by a slit in the outer layer 60 of the outer cover 26.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. For example, FIGS. 1 and 2 illustrate an absorbent body 34 that is rectangular in shape, with a first end edge 40 and second end edge 42 that are parallel to one another and the lateral axis 31. However, FIG. 7 illustrates a first end edge 40 of the absorbent body 34 that is curved. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10. The absorbent body 34 can have longitudinal side edges, 36 and 38, and front and back end edges, 40 and 42.

The absorbent body 34 can also be further configured to help the caregiver maintain control of the pocket 64 of the absorbent article 10. For example, the first end edge 40 of the absorbent body 34 can include at least one notch 41. In an embodiment depicted in FIG. 8, the first end edge 40 of the absorbent body 34 can include two notches 41. The notches 41 can be configured to provide a space for a caregiver's finger tips to rest when the caregiver is using the pocket 64 to wipe the wearer of the article 10. The notches 41 can be configured to be of any suitable size. The notches 41 can help provide the distance 82 between the first end edge 40 of the absorbent body 34 and the upper lateral edge 74 of the pocket 64 and the advantages previously discussed above with respect to the distance 82. In some embodiments, the location of the notch 41 or notches 41 can correspond to the only portion 74a of the upper lateral edge 74 of the pocket 64 that has the distance 82 between the first end edge 40 of the absorbent body 34 and the upper lateral edge 74 of the pocket 64 described above. In such an embodiment, the first end edge 40 of the absorbent body 34 could be substantially aligned with the upper lateral edge 74 of the pocket 64, except where one or more of the notches 41 were formed in the first end edge 40 of the absorbent body 34. Importantly, although the notches 41 are only shown with respect to FIG. 8, it can be appreciated that one or more notches 41 could be employed with any of the embodiments discussed herein.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

The absorbent body 34 can be superposed over the inner layer 62 of the outer cover 26 and can be bonded to the inner layer 62 of the outer cover 26, such as by being bonded thereto with adhesive. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In an embodiment, a layer, such as but not limited to, a fluid transfer layer (not shown), can be positioned between the absorbent body 34 and the outer cover 26.

Bodyside Liner:

The bodyside liner 28 of the absorbent article 10 can overlay the absorbent body 34 and the outer cover 26 and can isolate the wearer's skin from liquid waste retained by the absorbent body 34. In various embodiments, a fluid transfer layer (not shown) can be positioned between the bodyside liner 28 and the absorbent body 34. In various embodiments, an acquisition layer (not shown) can be positioned between the bodyside liner 28 and the absorbent body 34 or a fluid transfer layer, if present. In various embodiments, the bodyside liner 28 can be bonded to the acquisition layer, or to the fluid transfer layer if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer, if present, and/or an acquisition layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. The bodyside liner 28 may be narrower than the outer cover 26, but it is to be understood that the bodyside liner 28 and the outer cover 26 may be of the same dimensions, or that the bodyside liner 28 may be of greater width than the outer cover 26. It is also contemplated that the bodyside liner 28 may not extend beyond the absorbent body 34 and/or may not be secured to the outer cover 26. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 invented by Kirby, Scott S. C. et al. In a preferred embodiment, the bodyside liner 28 includes a bodyfacing surface that provides an uneven surface at least in the front waist region 12, such as a bodyfacing surface that includes projections as disclosed in U.S. Patent Application Publication No. 2014/0121623 noted above. Such a bodyfacing liner provides additional benefits in softness and assists in cleaning the wearer's skin when the caregiver uses the pocket 64 of the absorbent article 10 to wipe the wearer.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Leg Elastics:

Leg elastic members 56, 58 (labeled in FIGS. 1 and 2) can be secured to the outer cover 26, such as by being bonded thereto by laminate adhesive, generally laterally inward of the longitudinal side edges, 18 and 20, of the absorbent article 10. The leg elastic members 56, 58 can form elasticized leg cuffs 57, 59, respectively, that further help to contain body exudates. In an embodiment, the leg elastic members 56, 58 may be disposed between the inner layer 62 and outer layer 60 of the outer cover 26 or between other layers of the absorbent article 10. The leg elastic members 56, 58 can be a single elastic member, or each leg elastic member 56, 58 can include more than one elastic member, such as illustrated herein. A wide variety of elastic materials may be used for the leg elastic members 56, 58. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Of course, the leg elastic members 56, 58 can be omitted from the absorbent article 10 without departing from the scope of this disclosure.

Fastening System:

In an embodiment, the absorbent article 10 can include a fastener system. The fastener system can include one or more back fasteners 106 and one or more front fasteners 108, with only one front fastener 108 being shown in FIGS. 1, 2, and 4-7. Portions of the fastener system may be included in the front waist region 12, rear waist region 14, or both. The front fastener(s) 108 can be the same material as the pocket material 66, as shown in FIGS. 1, 2, and 4-7, however, the front fastener(s) 108 can be formed from a different material than the pocket material 66. For example, in FIG. 8, the front fastener 108 can be the garment facing surface 27 of the outer cover 26.

The fastener system can be configured to secure the absorbent article 10 about the waist of the wearer and maintain the absorbent article 10 in place during use. In an embodiment, the back fasteners 106 can include one or more materials bonded together to form a composite ear as is known in the art. For example, the composite fastener may be composed of a stretch component 110, a nonwoven carrier or hook base 112, and a fastening component 114.

Waist Elastic Members:

In an embodiment, the absorbent article 10 can have one or more waist elastic members, such as rear waist elastic member 52, which can be formed of any suitable elastic material. The rear waist elastic member 52 can be in a rear waist region 14 of the absorbent article 10. Suitable elastic materials for waist elastic members can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic member 52 can be omitted from the absorbent article 10 without departing from the scope of this disclosure.

EMBODIMENTS

Embodiment 1

An absorbent article including a front waist region including a front waist edge, a rear waist region including a rear waist edge, and a crotch region, the absorbent article further including a longitudinal axis and a lateral axis, the absorbent article comprising: an absorbent assembly including a bodyside liner, an outer cover, and an absorbent body disposed between the bodyside liner and the outer cover, the absorbent body including a first longitudinal edge, a second longitudinal edge opposite from the first longitudinal edge, a first end edge, and a second end edge, the first end edge being disposed in the front waist region; and a pocket disposed in the front waist region, the pocket including a first side edge, a second side edge opposite from the first side edge, an upper lateral edge, and a lower lateral edge, at least a portion of the upper lateral edge of the pocket being closer to the front waist edge than is the first end edge of the absorbent body, the pocket being closed with respect to the absorbent assembly at the first side edge, the second side edge, and the upper lateral edge and being open with respect to the absorbent assembly at the lower lateral edge.

Embodiment 2

An absorbent article including a front waist region including a front waist edge, a rear waist region including a rear waist edge, and a crotch region, the absorbent article further including a longitudinal axis and a lateral axis, the absorbent article comprising: an absorbent assembly including a bodyside liner, an outer cover, and an absorbent body disposed between the bodyside liner and the outer cover, the absorbent body including a first longitudinal edge, a second longitudinal edge opposite from the first longitudinal edge, a first end edge, and a second end edge, the first end edge being disposed in the front waist region; and a pocket disposed in the front waist region and having a pocket longitudinal axis that is substantially aligned with the longitudinal axis of the absorbent article, the pocket including a first side edge, a second side edge opposite from the first side edge, an upper lateral edge, and a lower lateral edge, the pocket being closed with respect to the absorbent assembly at the first side edge, the second side edge, and the upper lateral edge and being open with respect to the absorbent assembly at the lower lateral edge, the pocket having a width defined between the first side edge and the second side edge and having a length defined between the upper lateral edge and the lower lateral edge, the width being between about 3.00 inches and about 6.00 inches, the length being between about 1.25 inches and about 3.75 inches.

Embodiment 3

The absorbent article of embodiment 2, wherein at least a portion of the upper lateral edge of the pocket is closer to the front waist edge than is the first end edge of the absorbent body.

Embodiment 4

The absorbent article of embodiment 1 or embodiment 3, wherein a distance between the at least a portion of the upper lateral edge of the pocket and the first end edge of the absorbent body as measured in a direction parallel to the longitudinal axis is between about 0.25 inches and about 0.75 inches.

Embodiment 5

The absorbent article of embodiment 1, wherein the pocket includes a width defined between the first side edge and the second side edge and includes a length defined between the upper lateral edge and the lower lateral edge, the length being between about 1.25 inches and about 3.75 inches.

Embodiment 6

The absorbent article of embodiment 2 or embodiment 5, wherein the length is between about 2.00 inches and about 3.00 inches.

Embodiment 7

The absorbent article of any one of embodiments 1 or 3-6, wherein the width is between about 3.00 inches and about 6.00 inches.

Embodiment 8

The absorbent article of any of the preceding embodiments, wherein the width is between about 3.50 inches and about 4.50 inches.

Embodiment 9

The absorbent article of any one of the preceding embodiments, wherein the absorbent article further includes a first longitudinal side edge and a second longitudinal side edge, the first longitudinal side edge and the second longitudinal side edge each extending between the front waist edge and the rear waist edge, and wherein at least a portion of the first side edge of the pocket is closer to the first longitudinal side edge of the absorbent article than is the first longitudinal edge of the absorbent body in the front waist region.

Embodiment 10

The absorbent article of embodiment 9, wherein at least a portion of the second side edge of the pocket is closer to the second longitudinal side edge of the absorbent article than is the second longitudinal edge of the absorbent body in the front waist region.

Embodiment 11

The absorbent article of any one of the preceding embodiments, wherein the pocket includes a pocket material that is coupled to the outer cover.

Embodiment 12

The absorbent article of embodiment 11, the absorbent article further comprising: a fastening system including a pair of rear fasteners and at least one front fastener in the front waist region; wherein the pocket material forms the at least one front fastener.

Embodiment 13

The absorbent article of any one of the preceding embodiments, wherein the outer cover includes an inner layer and an outer layer, and wherein the pocket is formed where the inner layer is not coupled to the outer layer and the second lateral edge of the pocket is formed by a slit in the outer layer.

Embodiment 14

The absorbent article of any one of the preceding embodiments, wherein all of the upper lateral edge of the pocket is closer to the front waist edge than is the first end edge of the absorbent body.

Embodiment 15

The absorbent article of any one of the preceding embodiments, wherein the first lateral edge of the absorbent body is substantially parallel to the lateral axis of the absorbent article.

Embodiment 16

The absorbent article of any one of the preceding embodiments, wherein the upper lateral edge of the pocket is substantially parallel to the lateral axis of the absorbent article.

Embodiment 17

The absorbent article of any one of the preceding embodiments, wherein the first lateral edge of the absorbent body is curved.

Embodiment 18

The absorbent article of any one of the preceding embodiments, wherein the first side edge of the pocket and the second side edge of the pocket are each substantially aligned with the longitudinal axis of the absorbent article.

Embodiment 19

The absorbent article of any one of the preceding embodiments, wherein the first end edge of the absorbent body includes at least one notch.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a front waist region including a front waist edge, a rear waist region including a rear waist edge, and a crotch region, the absorbent article further including a longitudinal axis and a lateral axis, the absorbent article comprising:

an absorbent assembly including a bodyside liner, an outer cover, and an absorbent body disposed between the bodyside liner and the outer cover, the absorbent body including a first longitudinal edge, a second longitudinal edge opposite from the first longitudinal edge, a first end edge, and a second end edge, the first end edge being disposed in the front waist region;

a fastening system including a pair of rear fasteners and at least one front fastener in the front waist region; and a pocket material coupled to the outer cover in the front waist region and forming the at least one front fastener, the pocket material having an upper edge, a lower edge, and two side edges, and the pocket material forming a pocket disposed in the front waist region, the pocket including a first pocket side edge and a second pocket side edge opposite from the first pocket side edge, the pocket material upper edge forming a pocket upper lateral edge and the pocket material lower edge forming a pocket lower lateral edge, at least a portion of the pocket upper lateral edge being closer to the front waist edge than is the first end edge of the absorbent body, the pocket being closed with respect to the absorbent assembly at the first pocket side edge, the second pocket side edge, and the pocket upper lateral edge and being open with respect to the absorbent assembly at the pocket lower lateral edge.

2. The absorbent article of claim 1, wherein a distance between the at least a portion of the pocket upper lateral edge and the first end edge of the absorbent body as measured in a direction parallel to the longitudinal axis is between about 0.25 inches and about 0.75 inches.

3. The absorbent article of claim 1, wherein the pocket includes a width defined between the first pocket side edge and the second pocket side edge and includes a length defined between the pocket upper lateral edge and the pocket lower lateral edge, the length being between about 1.25 inches and about 3.75 inches.

4. The absorbent article of claim 3, wherein the length is between about 2.00 inches and about 3.00 inches.

5. The absorbent article of claim 3, wherein the width is between about 3.00 inches and about 6.00 inches.

6. The absorbent article of claim 5, wherein the width is between about 3.50 inches and about 4.50 inches.

7. The absorbent article of claim 6, wherein the length is between about 2.00 inches and about 3.00 inches.

8. The absorbent article of claim 1, wherein the absorbent article further includes a first longitudinal side edge and a second longitudinal side edge, the first longitudinal side edge and the second longitudinal side edge each extending between the front waist edge and the rear waist edge, and wherein at least a portion of the first pocket side edge is closer to the first longitudinal side edge of the absorbent article than is the first longitudinal edge of the absorbent body in the front waist region.

9. The absorbent article of claim 8, wherein at least a portion of the second pocket side edge is closer to the second longitudinal side edge of the absorbent article than is the second longitudinal edge of the absorbent body in the front waist region.

10. The absorbent article of claim 1, wherein all of the pocket upper lateral edge is closer to the front waist edge than is the first end edge of the absorbent body.

11. The absorbent article of claim 1, wherein the first lateral edge of the absorbent body is substantially parallel to the lateral axis of the absorbent article.

12. The absorbent article of claim 11, wherein the pocket upper lateral edge is substantially parallel to the lateral axis of the absorbent article.

13. The absorbent article of claim 1, wherein the first lateral edge of the absorbent body is curved.

14. The absorbent article of claim 13, wherein the first pocket side edge and the second pocket side edge are each substantially aligned with the longitudinal axis of the absorbent article.

15. The absorbent article of claim 1, wherein the first end edge of the absorbent body includes at least one notch.

16. The absorbent article of claim 1, wherein at least a portion of the pocket lower lateral edge is further away from the front waist edge than is the first end edge of the absorbent body.

17. An absorbent article including a front waist region including a front waist edge, a rear waist region including a rear waist edge, and a crotch region, the absorbent article further including a longitudinal axis and a lateral axis, the absorbent article comprising:

an absorbent assembly including a bodyside liner, an outer cover, and an absorbent body disposed between the bodyside liner and the outer cover, the absorbent body including a first longitudinal edge, a second longitudinal edge opposite from the first longitudinal edge, a first end edge, and a second end edge, the first end edge being disposed in the front waist region;

a fastening system including a pair of rear fasteners and at least one front fastener in the front waist region; and a pocket material coupled to the outer cover in the front waist region and forming the at least one front fastener, the pocket material having an upper edge, a lower edge, and two side edges, and the pocket material forming a pocket disposed in the front waist region and having a pocket longitudinal axis that is substantially aligned with the longitudinal axis of the absorbent article, the pocket including a first pocket side edge and a second pocket side edge opposite from the first pocket side edge, the pocket material upper edge forming a pocket upper lateral edge and the pocket material lower edge forming a pocket lower lateral edge, the pocket being closed with respect to the absorbent assembly at the first pocket side edge, the second pocket side edge, and the pocket upper lateral edge and being open with respect to the absorbent assembly at the pocket lower lateral edge, the pocket having a width defined between the first pocket side edge and the second pocket side edge and having a length defined between the pocket upper lateral edge and the pocket lower lateral edge, the width being between about 3.00 inches and about 6.00 inches, the length being between about 1.25 inches and about 3.75 inches.

18. The absorbent article of claim 17, wherein at least a portion of the pocket upper lateral edge is closer to the front waist edge than is the first end edge of the absorbent body.

19. The abosrbent article of claim 18, wherein at least a portion of the pocket lower lateral edge is further away from the front waist edge than is the first end edge of the absorbent body.

* * * * *